(12) United States Patent
Dischler (10) Patent No.: US 6,585,693 B1
(45) Date of Patent: Jul. 1, 2003

(54) BLISTER SYRINGE WITH OPTIONAL BIFURCATED GUARD

(76) Inventor: Louis Dischler, 252 W. Park Dr. Duncan Park, Spartanburg, SC (US) 29306-5013

( * ) Notice: Subject to any disclaimer, the term of this patent is extended or adjusted under 35 U.S.C. 154(b) by 0 days.

(21) Appl. No.: 09/918,411

(22) Filed: Jul. 30, 2001

(51) Int. Cl.⁷ .................................. A61M 5/00
(52) U.S. Cl. ................. 604/171; 604/185; 604/198; 604/200; 604/217
(58) Field of Search .................. 604/110, 111, 604/171, 181–183, 185, 187, 192, 195, 197–202, 212, 217, 244, 263; 420/542.8

(56) References Cited

U.S. PATENT DOCUMENTS 3,736,933 A * 6/1973 Szabo ...................... 604/200
4,935,011 A * 6/1990 Hogan ...................... 604/177
5,120,321 A * 6/1992 Oksman et al. ............. 604/198
5,810,783 A * 9/1998 Claro ....................... 604/199
5,873,860 A * 2/1999 Kahlert ..................... 604/217
5,931,815 A * 8/1999 Liu ......................... 604/171

* cited by examiner

Primary Examiner—Ira S. Lazarus
Assistant Examiner—Andrea M. Ragonese (57) ABSTRACT

The present invention provides a unitary syringe having a mounted needle surrounded by a sheath having a break-zone. The fluid medicament to be injected is contained within a blister cavity formed between upper and lower polymeric layers. Accidental needle sticks are reduced by optional guard fingers surrounding the needle. These fingers extend past the and bracket the sharpened end of the needle.

28 Claims, 8 Drawing Sheets

BLISTER SYRINGE WITH OPTIONAL BIFURCATED GUARD

FIELD OF THE INVENTION

The following invention relates generally to single dose syringe and its method of use. More specifically, it relates to a blister syringe having an integral needle with a sheath having a break-zone, with an optional integrity indicator, guard fingers, and secondary prep blister.

BACKGROUND OF THE INVENTION

There is a need for an inexpensive syringe that may be conveniently manufactured and preloaded with a single dose of injectable fluid. Preferably, such a syringe should be unitary and self-contained, comprising all of the elements needed for performing an injection. In addition, such a syringe would preferably have a built-in safety element in order to reduce the chance of accidental needle sticks and the transfer of blood-borne pathogens such as AIDS and hepatitis. Such a safety element should function automatically. Another desirable safety element would be an indicator to insure the integrity of the preloaded dose.

SUMMARY OF THE INVENTION

The present invention provides a unitary syringe having a mounted needle surrounded by a sheath having a break-zone. The fluid medicament to be injected is contained within a blister cavity formed between upper and lower polymeric layers, and is in fluid communication with the needle. It is preferred that the blister cavity be fully filled with the fluid, and substantially free of non-dissolved gas. The sheath may be formed from the same upper and lower polymeric layers forming the blister cavity, or it may be supplied as a pre-form with the needle.

The syringe may be manufactured as a single unit, but it is preferred that the syringe be formed as an array, generally a linear array, held together by tabs, or preferably by a thinned web of at least one of the polymeric layers. The web should be thin enough to be easily torn or broken by the user. Typically, a twisting motion would be used to separate an individual syringe from an array of syringes.

The polymeric layer comprises one or more polymeric lamina. A sealable lamina may be used with a barrier lamina, for instance. Such multilayer polymeric constructions are well known. Polymers that may be used for the polymeric barrier layer include ethylene/vinyl alcohol copolymer (EVOH), polyvinylidene chloride (PVDC) and polyacrylonitrile (PAN). These polymers are exemplary only, and any polymeric or other flexible material may be used as a barrier consistent with the stability of the medicament, the storage time required, compatibility with the medicament, and any other particular requirements. While polymeric barrier lamina or layers are preferred, the film may be metallized with aluminum or other metals to improve the barrier properties, however, it is preferred that the optical depth of the metallized coating does not prevent visual inspection of the contents. Exemplary polymers that may serve as sealable lamina, and in some cases as a barrier also, are polyethelene, polypropylene, polycarbonate, nylon, polyester, PVC, EVA and copolymers and blends of the above. Any other suitable heat sealable polymer may be used.

Filling of the blister cavity by way of a fill canal is preformed from the needle (distal) end of the syringe, or from the blister (proximal) end. A plug is inserted into the fill canal or, preferably, the walls of the canal are collapsed to seal off the syringe. In the latter case, sealing is preferably by application of ultrasonic pressure horn or pin. When an array of syringes is formed, the blister cavities may be gang filled from a central port via runners to the fill canals, with the runners later trimmed and discarded. Preferably, a vacuum is drawn to collapse the blisters, and the fill fluid is then introduced under pressure.

The integrity of the blister cavity can be assured by an optional indicator in at least one of the layers forming the blister walls. Such an indicator would typically be molded with an outer concave surface. When filled with an internal cavity pressure greater than atmospheric, the indicator would invert, becoming convex. Breaking the break-zone of the sheath or any other communication of the cavity with the environment would allow leakage of the fluid resulting in the indicator returning to its favored molded convex form. It is preferred that the indicator be placed generally in the center of the blister wall to provide a tactile indication to the user.

Accidental needle sticks can be reduced by optional guard fingers surrounding the needle. These fingers extend past the distal (sharpened) end of the needle, and substantially lie in a first plane (the syringe plane) with the needle tip. The tips of the fingers make first contact with the target surface to be injected. The user then directs the syringe in a second plane (the injection plane, substantially perpendicular to the syringe plane) whereby the finger guards are flexibly and reversibly bent, allowing the needle tip to encounter the target surface. The user then directs the syringe forward along the axis of the needle to insert the needle into the target surface. A "Z" motion is transcribed by the needle tip during the insertion process.

Injection of the fluid is performed by squeezing the blister between two fingers, generally the thumb and index fingers. Optionally, the first wall of the blister cavity may be made bistable, with the second wall more rigid, so that upon inversion of the first wall the first wall closely fits the mating second wall, thereby driving most of the fluid from the cavity.

A syringe may comprise a second blister cavity (sans sharpened needle) for application of an injection prep such as alcohol or other sterilizing fluid. In this way, everything needed for the injection is self-contained in a unitary syringe. The second blister cavity need not be fully filled.

It is an object of the present invention, therefore, to provide a single dose fully sealed syringe comprising a needle having an integral sheath having a break-zone, wherein the needle is in fluid communication with a blister cavity formed between a first and a second layer, and wherein at least one of the layers is flexible.

It is another object of at least one embodiment of the present invention to provide an array of single dose fully sealed syringes, joined by separable webs or tabs.

It is another object of at least one embodiment of the present invention to provide a single dose safety syringe having guard fingers extending past the needle tip.

It is another object of at least one embodiment of the present invention to provide a single dose fully sealed syringe having an integrity indicator on a wall of a blister cavity containing an injectable fluid medicament.

BRIEF DESCRIPTION OF THE DRAWINGS

The above as well as other objects of the invention will become more apparent from the following detailed description of the preferred embodiments of the invention, when taken together with the accompanying drawings in which.

DETAILED DESCRIPTION OF THE PRESENTLY PREFERRED EMBODIMENTS

The drawings constitute a part of this specification and include exemplary embodiments to the invention, which may be embodied in various forms. It is to be understood that in some instances various aspects of the invention may be shown exaggerated or enlarged to facilitate an understanding of the invention. Specific details disclosed herein are not to be interpreted as limiting, but rather as a basis for the claims and as a representative basis for teaching one skilled in the art to employ the present invention in virtually any appropriately detailed system, structure or manner.

Figure 1:
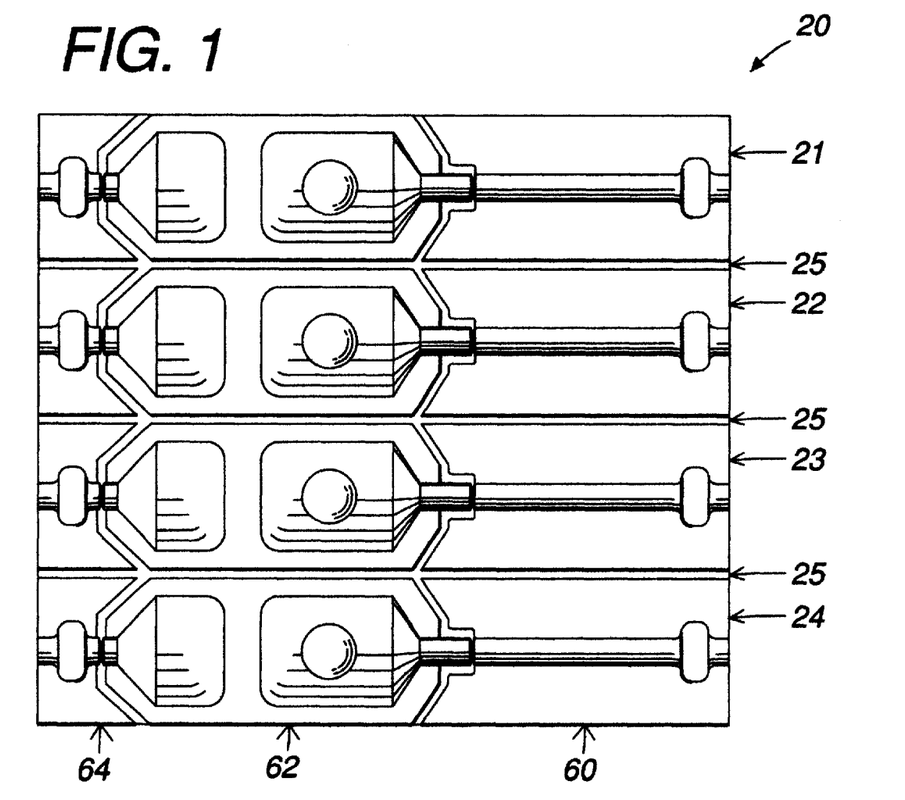
FIG. 1 is a plan view of an array of unitary syringes according to one embodiment of the invention.

Referring now to the drawings wherein like numerals refer to like parts, FIG. 1 illustrates an array 20 of individual syringes 21, 22, 23, 24, joined together by thin webs 25. Individual syringe 24 comprises syringe body 62, needle sheath 60, and prep cap 64.

Figure 2A:
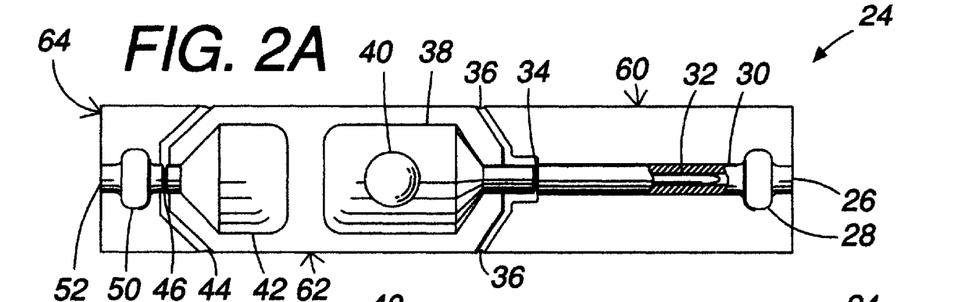
FIG. 2A is a plan view of one syringe broken from the array shown in FIG. 1.

FIG. 2A illustrates unit syringe 24 released by bending or twisting to break or tear web 25 (shown in FIG. 1). Syringe body 62 comprises indicator button 40 shown in the safe, or convex position, a first blister chamber 38 for fluid medicament, needle 32, and second blister chamber 42 for prep fluid. Second blister chamber 42 is closed by cap 64, which comprises fill port 52, seal 50, and break-zone 46. The cap 64 is joined to syringe body 62 by thin web 44, which can be broken by twisting or bending, allowing fluid contained within second blister chamber 42 to escape at breakzone 46. Needle sheath 60 is joined similarly to syringe body 62 by way of thin web 36, which can be broken by twisting. Break-zone 34 is also parted by such twisting action, allowing needle chamber 30 to be withdrawn from needle 32. Filling of chamber 38 is accomplished via fill port 26, and through needle 32, which is in fluid communication with chamber 38. Subsequently the fill port is closed by seal 28, which may be accomplished by application of a hot pin, but preferably by the pressure application of an ultrasonically vibrated horn or pin (not shown).

Figure 2B:
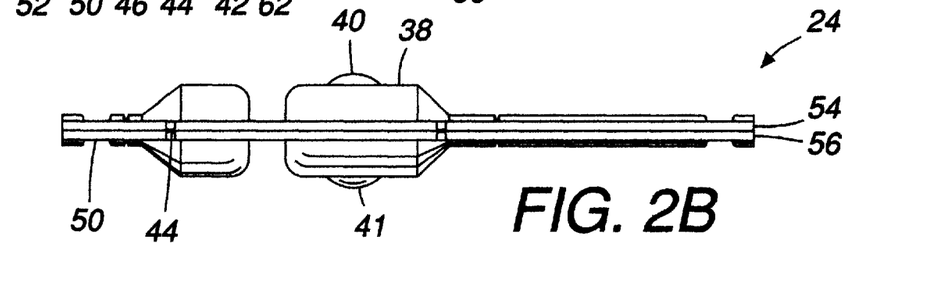
FIG. 2B is a side view of the syringe shown in FIG. 2A.

FIG. 2B illustrates the side view of unit syringe 24, formed of layers 54, 56. Indicators 40, 41 are shown in the safe or convex form. While these indicators are shown to be spherical, any geometry may be used, such as oval, elliptical, polygonal, etc., only constrained by the need for the blister to flatten or invert when the internal pressure contained within blister 38 is released, as would happen when accidental leakage occurs, indicating to the user that the integrity of the syringe 24 had been compromised.

Figure 3:
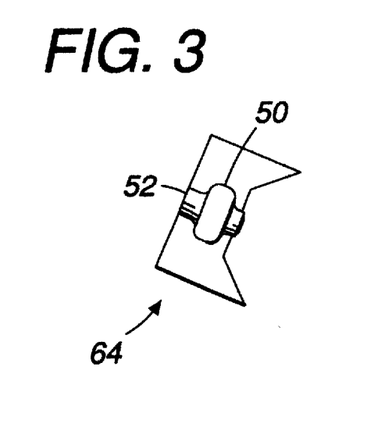
FIG. 3 is a plan view of a discarded cap from the syringe shown in FIG. 2A.
Figure 4:
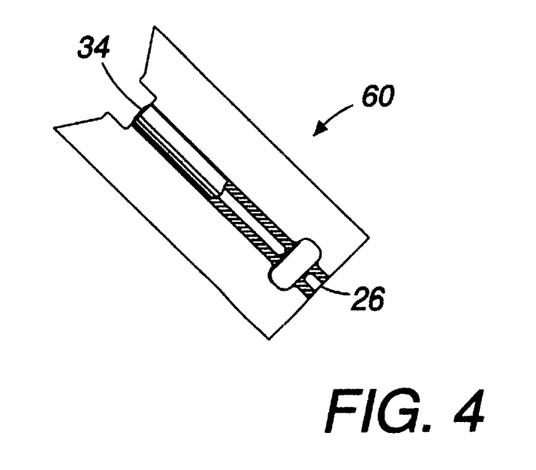
FIG. 4 is a plan view of a discarded sheath from the syringe shown in FIG. 2A.

In FIG. 3, discarded cap 64 is shown separated from unit syringe 24 (FIG. 2A), and in FIG. 4, discarded needle sheath 60 is shown similarly separated from unit syringe 24 at break-zone 34.

Figure 5A:
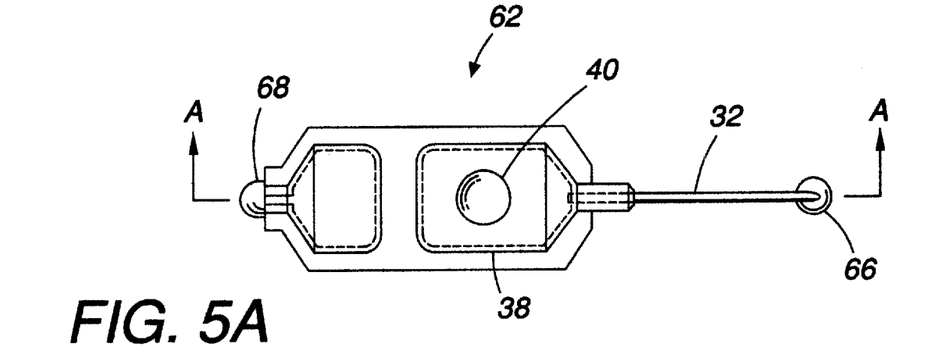
FIG. 5A is a plan view of the syringe shown in FIG. 2A, after removal of the cap and sheath in preparation for use.
Figure 5B:
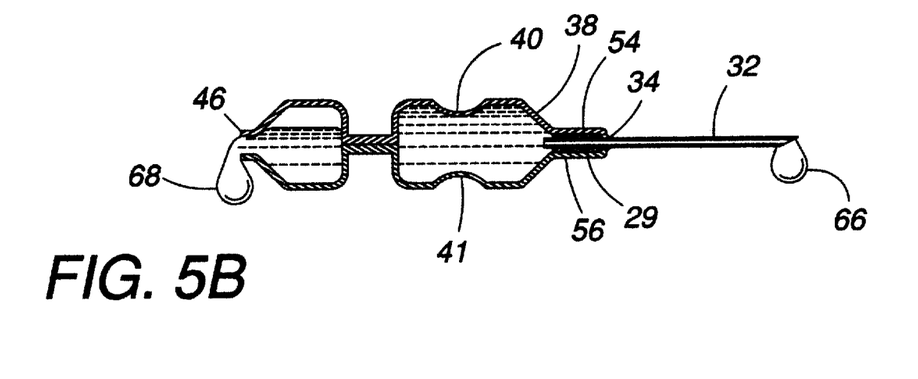
FIG. 5B is a cross-sectional view of the syringe shown in FIG. 5A, taken along line A—A.

With needle sheath and cap discarded, syringe body 62 is shown in FIGS. 5A and 5B as ready for use. Prep fluid 68 is shown exiting from break-zone 46, and a drop of medicament 66 is shown at the sharpened tip of needle 32. Indicators 40, 41 have inverted and assumed a concave form. Needle 32 is sealed in fluid communication with cavity 38 by needle base preform 29, which is sealed between upper layer 54 and lower layer 56. These layers also form breakzone 34.

In FIGS. 6A, 6B, 6C, 6D, another embodiment of the instant invention is shown. Unit syringe 80 comprises syringe body 97 having guard fingers 94, 96 extending beyond the distal tip 33 of needle 32. Guard fingers 94, 96 are attached by a thin and easily broken web 87 to needle sheath 86, and optionally web 87 may be absent. Separable needle sheath 86 comprises fill port 83 and plug 81, sealably engaged with the internal diameter of needle chamber 30. A reduced diameter break-zone 34 insures that needle sheath 86 may be parted by twisting from syringe body 97. Separable prep unit 82, when broken from unit syringe 80 at break-zone 99, supplies prep fluid 68.

Figures 6A, 6B, 6C:
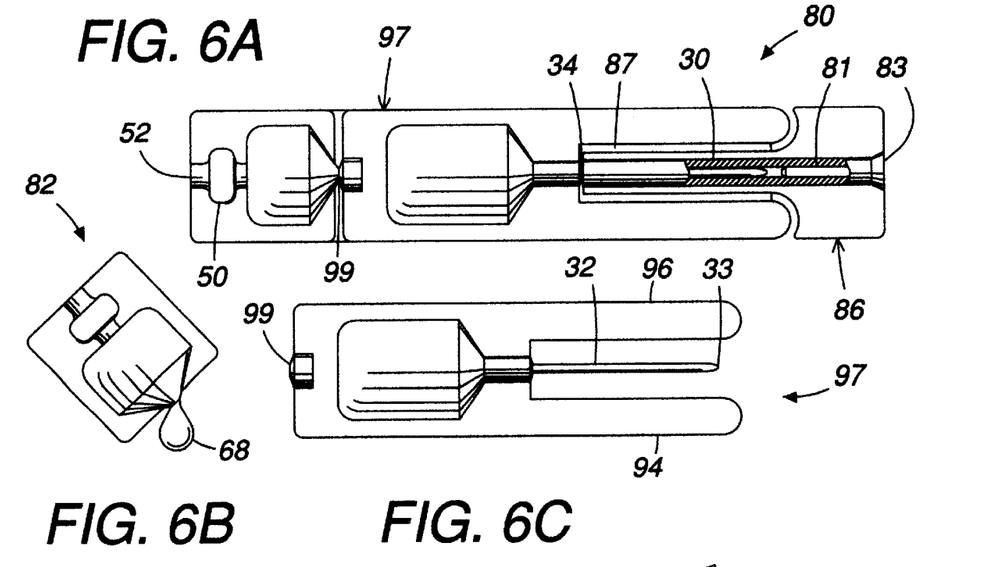
FIG. 6A is a plan view of a unitary syringe according to another embodiment of the invention.
FIG. 6B is a plan view of the prep container broken from the unitary syringe shown in FIG. 6A.
FIG. 6C is a plan view of the syringe shown in FIG. 6A, sans cap and sheath.
Figures 6D, 7:
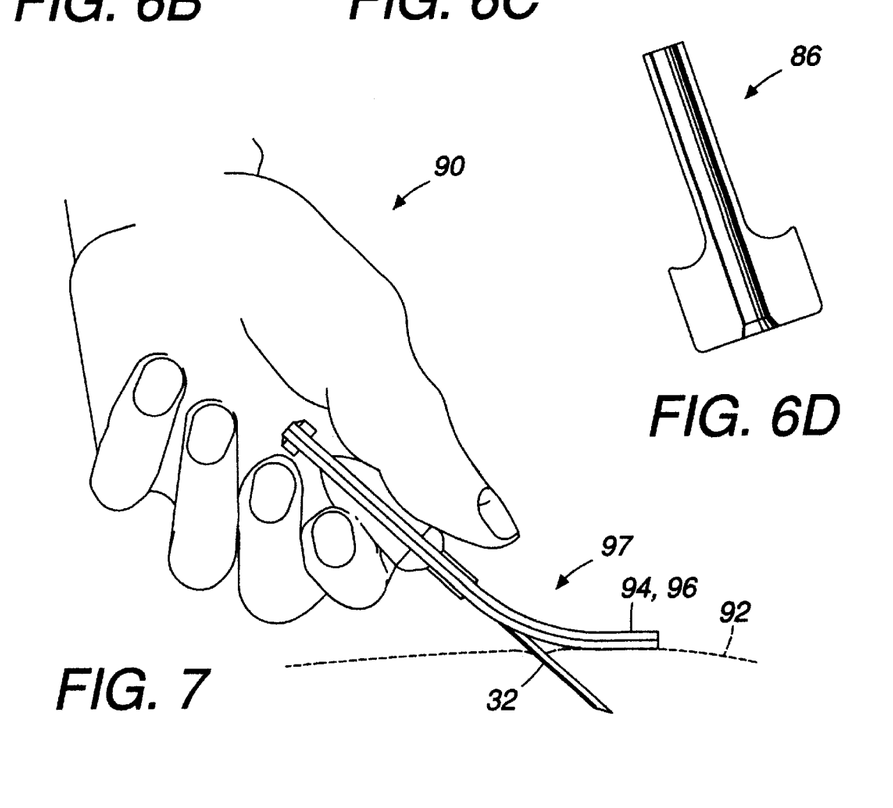
FIG. 6D is a plan view of the sheath broken from the unitary syringe shown FIG. 6A.
FIG. 7 is a side view of the syringe shown in FIG. 6C, shown in use.

In FIG. 7, the use of syringe body 97 by one hand 90 of the user to inject fluid beneath surface 92 is shown. Fingers 94, 96 are flexed during the injection, but spring back to a protective position surrounding the needle 32 when the injection procedure is completed.

Figure 8:
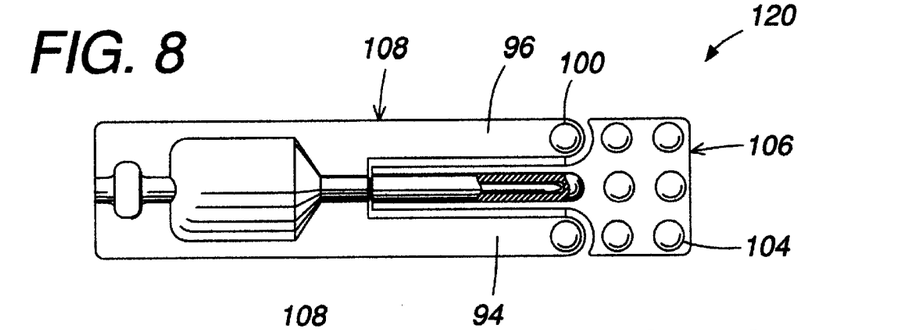
FIG. 8 is a plan view of a syringe according to another embodiment of the invention.

Turning now to FIG. 8, an alternative embodiment of the instant invention is shown. Unit syringe 120 is comprised of syringe body 108 and needle sheath 106 having finger grips 104. Guard fingers 94, 96 terminate at the distal end with hemispherical knobs 100.

Figure 9A:
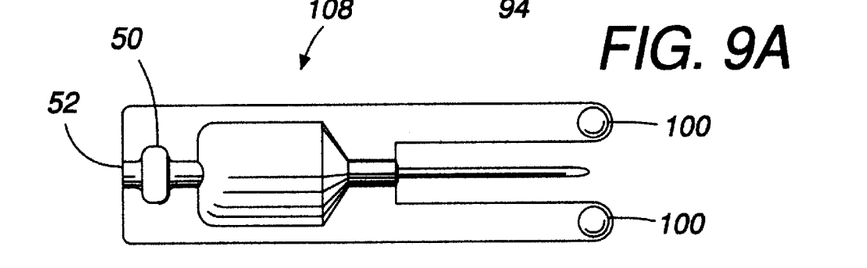
FIG. 9A is a plan view of the syringe shown FIG. 8, sans sheath.
Figure 9B:
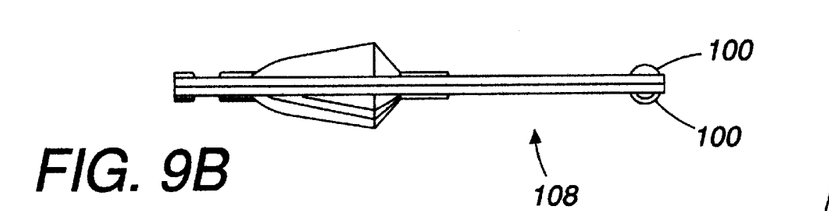
FIG. 9B is a side view of the syringe shown FIG. 9A.
Figure 9C:
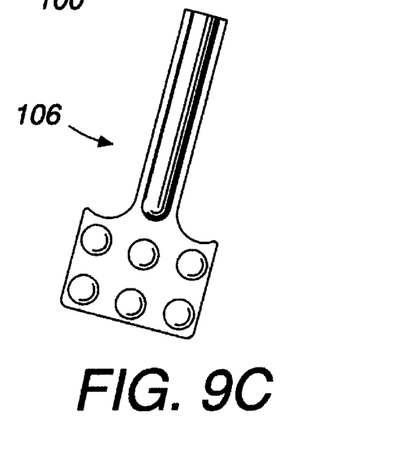
FIG. 9C is a plan view of the sheath broken from the syringe shown in FIG. 8.
Figure 10:
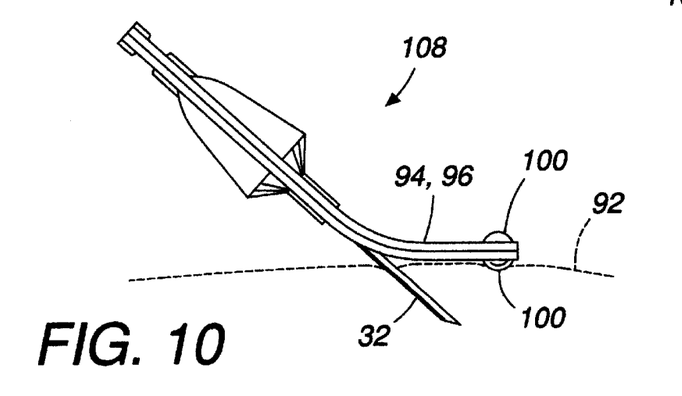
FIG. 10 is a side view of the syringe shown in FIG. 9B, shown in use.

In FIGS. 9A, 9B, syringe body 108 is shown ready for use, with discarded syringe sheath 106 shown in FIG. 9C. In FIG. 10, the lower of knobs 100 are shown to cooperate to improve the sliding of finger guards 94, 96 on the skin, and add additional dimensional protection to the needle 32 subsequent to injection after returning to the original unflexed condition.

Figure 11:
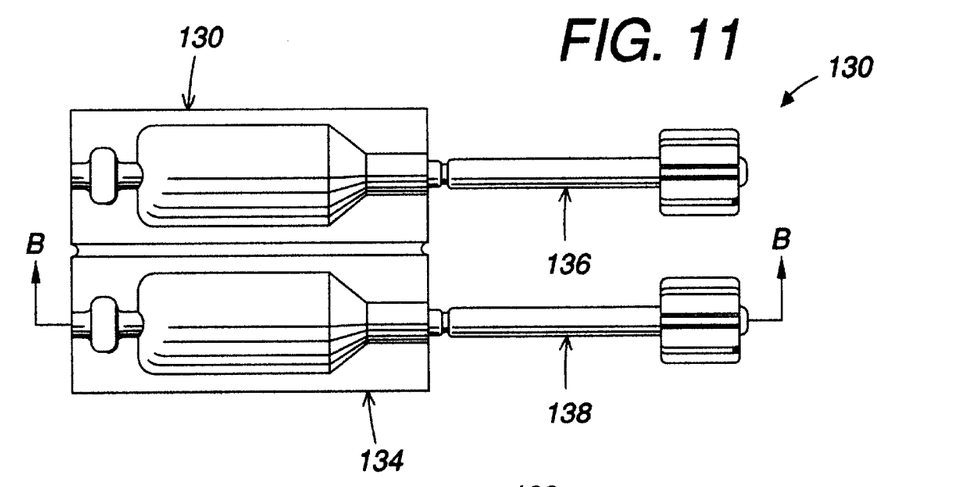
FIG. 11 is a plan view of a syringe array according to another embodiment of the invention.
Figure 12A:
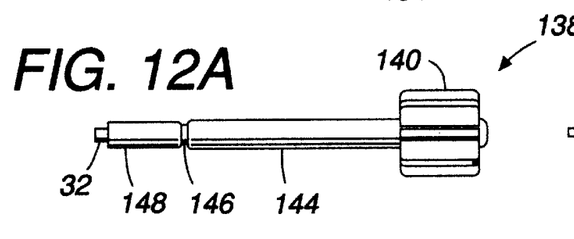
FIG. 12A is a side view of a sheath according to another embodiment of the invention.
Figure 12B:
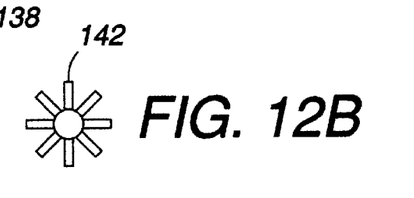
FIG. 12B is an end view of the sheath shown in FIG. 12A.
Figure 13A:
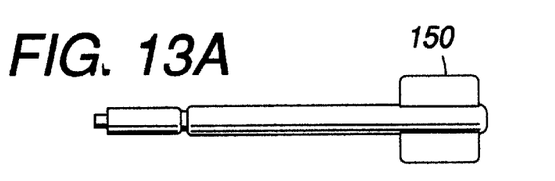
FIG. 13A is a side view of a sheath according to another embodiment of the invention.
Figure 13B:
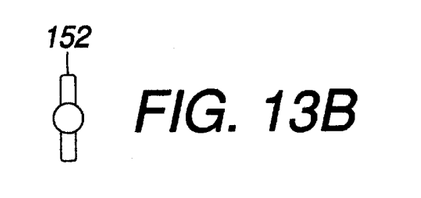
FIG. 13B is an end view of the sheath shown in FIG. 13B.
Figure 14:
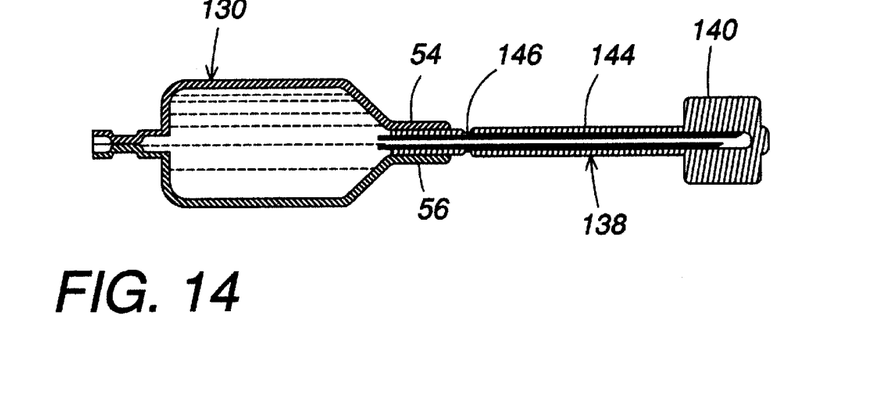
FIG. 14 is a cross-sectional view of one syringe shown in FIG. 11, taken along line B—B.

Turning now to FIG. 11, an alternative embodiment of the instant invention is shown as an array 130 comprising two unit syringes, comprising syringe bodies 130, 134, and preformed needle sheaths 136, 138, respectively. Preformed needle sheath 138 is shown separately in a side view in FIG. 12A, and in an end view in FIG. 12B. Distal end 140 comprises tab-like projections 142 for gripping and twisting, so as to part sheath 138 at break-zone 146, leaving proximal sheath base 148 and needle 32 fixed in the syringe body. An alternative needle sheath is shown in side and end views in FIGS. 13A and 13B respectively, and comprises two projections 152 for gripping and twisting, in order to produce a flatter profile. Any appropriate or decorative finger gripping geometry may be used. A cross-sectional view of an individual syringe taken along line B—B is shown in FIG. 14, wherein needle sheath 138 is sealably bonded to syringe body 130 by layers 54, 56 which also comprise syringe body 130.

Figure 15:
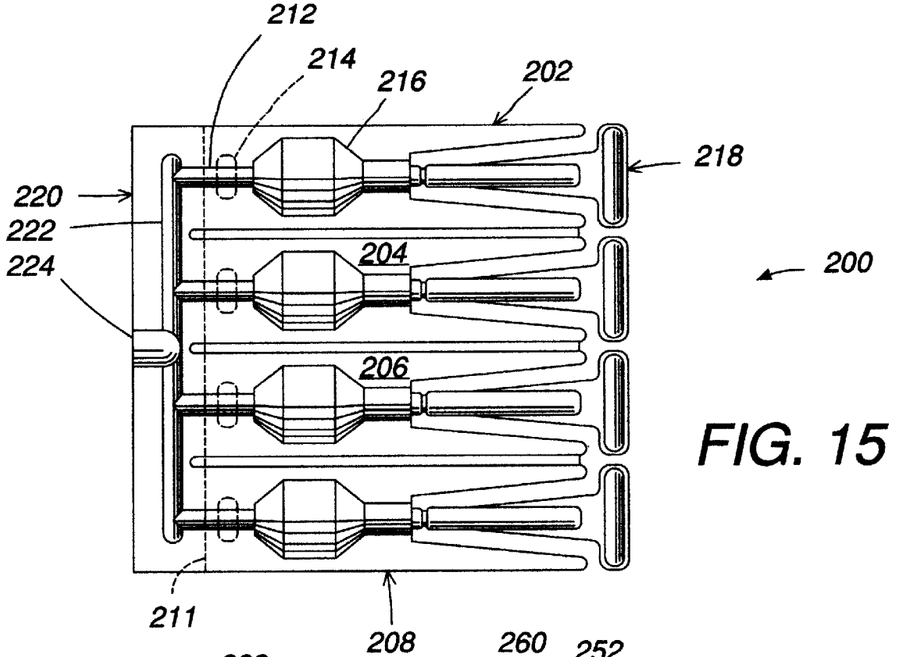
FIG. 15 is a plan view of an array of unitary syringes and runners, according to another embodiment of the invention.

In FIG. 15, an embodiment of the instant invention is shown wherein an array 200 of individual syringes 202, 204, 206, 208 joined together is illustrated. Each of the syringes is filled from a common source; for instance, cavity 216 is filled via runner 212 from common supply runner 222 from port 224. After filling, runner 212 is sealed in area 214, and the runners are trimmed on line 211. Portion 220 to the left of line 211 is discarded. Preform syringe sheath 218 is shown attached to syringe 202.

Figure 16:
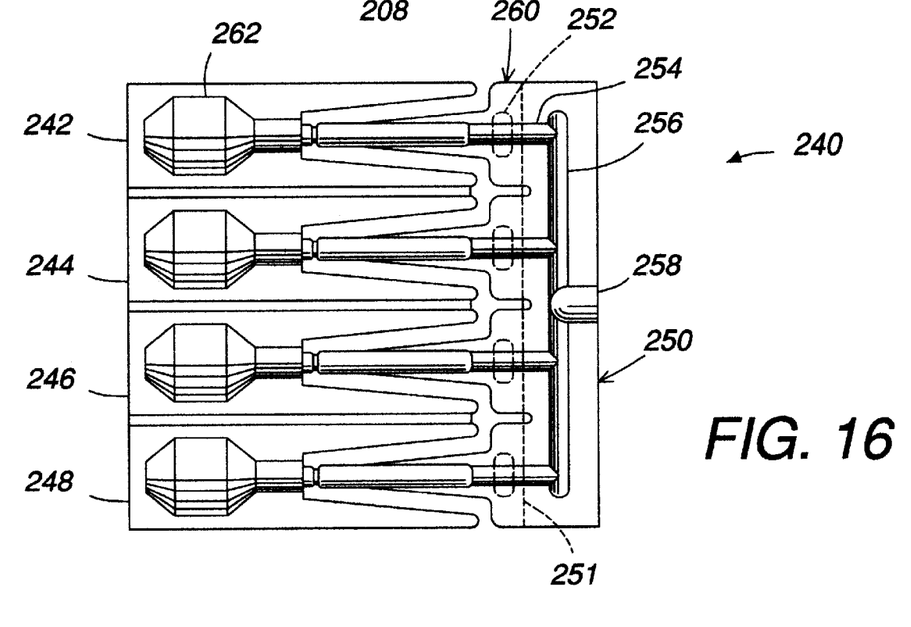
FIG. 16 is a plan view of an array of unitary syringes and runners, according to another embodiment of the invention.

An alternative embodiment is shown in FIG. 16, wherein the array 240 comprises individual syringes 242, 244, 246, 248 joined together and filled from the distal (needle) end; i.e., blister cavity 262 is filled via runner 254 via common supply runner 256 and ultimately by port 258, which would be in fluid communication with a supply of fluid medicament during filling (not shown). Runner 254 is then sealed in area 252, and the runners are trimmed on line 251 to produce the finished array with runner section 250 to the right of line 251 discarded, leaving needle sheath 260 to the left of line 251 attached to syringe 242.

Figure 17A:
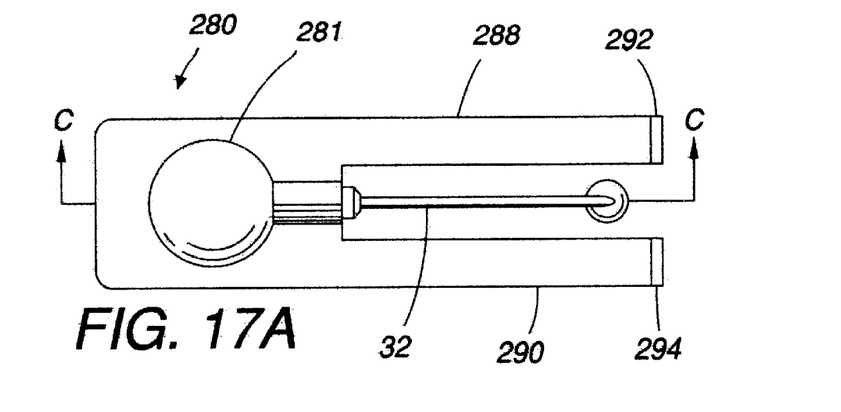
FIG. 17A is a plan view of a syringe according to another embodiment of the invention.
Figure 17B:
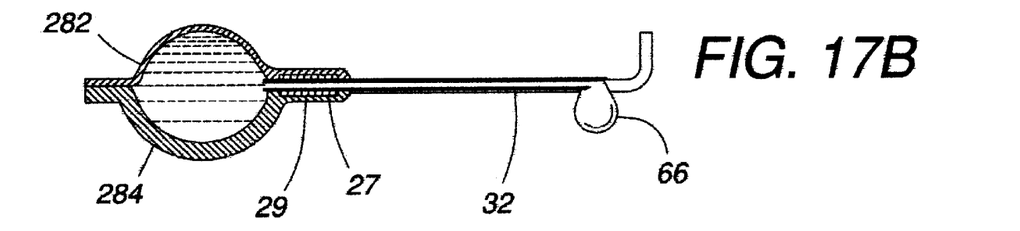
FIG. 17B is a cross-sectional view of the syringe shown in FIG. 17A, taken along line C—C.

Turning now to FIG. 17A, and FIG. 17B, which is a cross-section taken along line C—C of FIG. 17A; syringe 280 is shown after removal of the needle sheath (not shown). The blister cavity 281 comprises an invertible portion 282 and a more rigid portion 284. Guard fingers 288, 290 have extended bent sections 292, 294 in order to enhance the shielding of the needle 32 and to improve the sliding of the guards on the target skin surface.

Figure 18A:
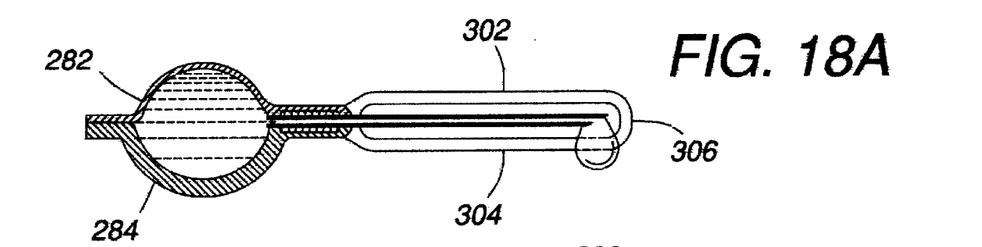
FIG. 18A is a cross-sectional view of a syringe according to another embodiment of the invention.
Figure 18B:
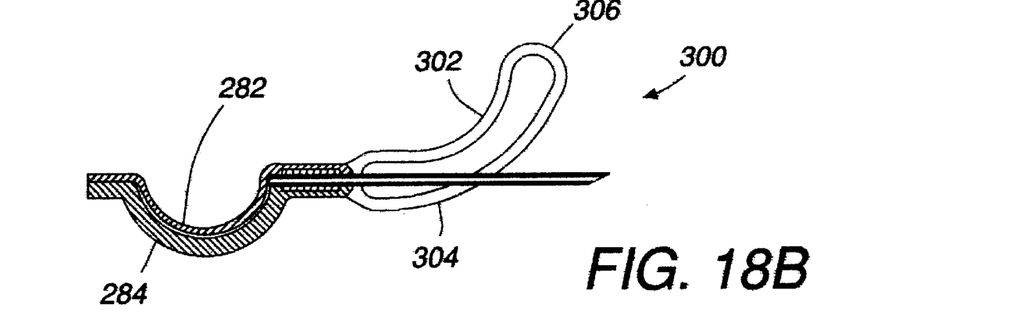
FIG. 18B is a cross-sectional view of the syringe shown in FIG. 18A, with guards flexed for injection.

An alternative embodiment of the guard fingers is shown in FIGS. 18A and 18B, wherein the guards are comprised of upper leg 302 and lower leg 304, joined at distal end 306, thereby enhancing the resistance to bending when the guards are pressed from the distal end, while still allowing easy bending of the guards during use. In FIG. 186, the blister cavity of syringe 300 is shown in the dispensed condition with invertible portion 282 in the final inverted position, and the guard fingers in the flexed, or injection position.

Figures 19A, 19B, 20:
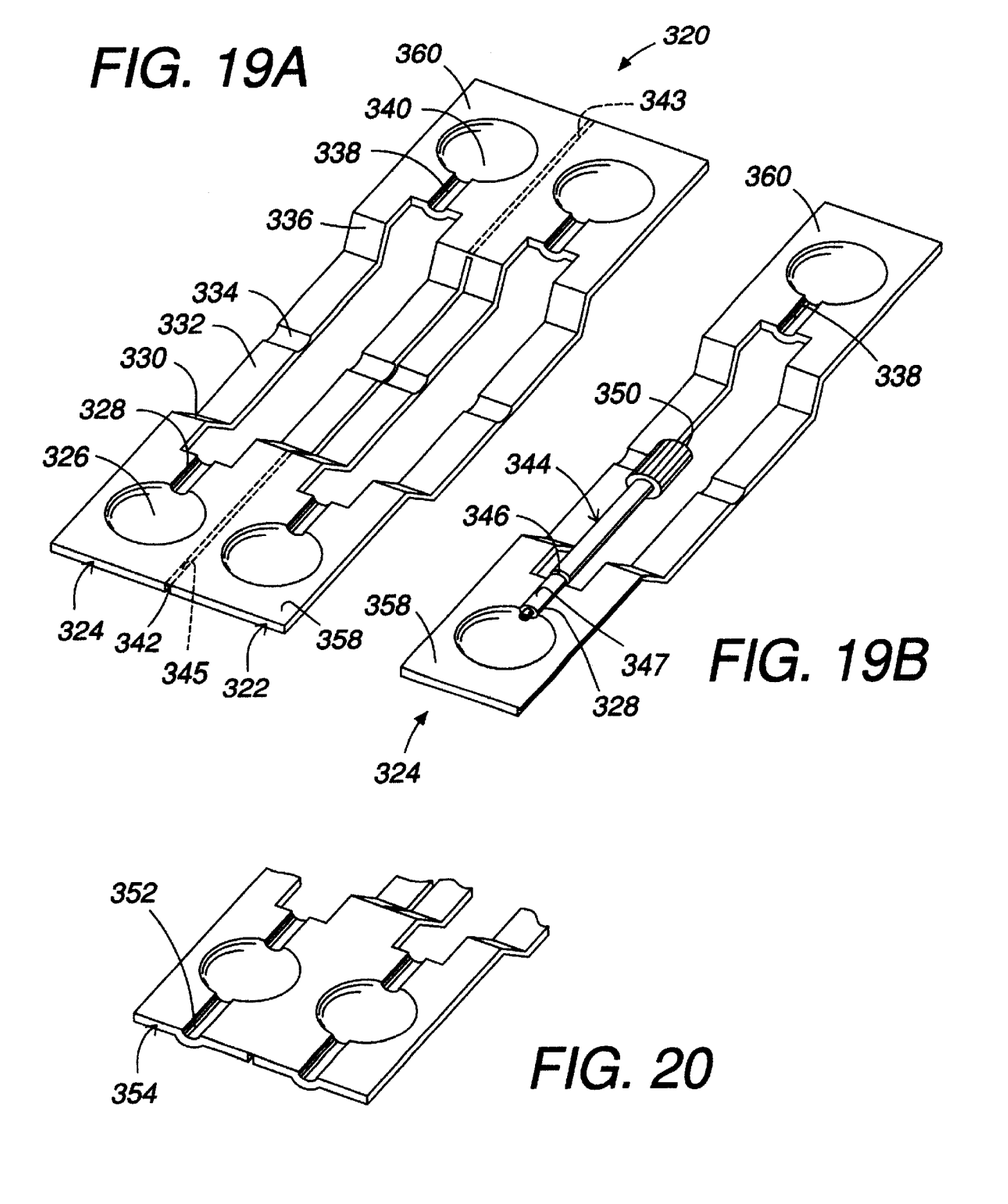
FIG. 19A is a perspective view of a syringe body preform array.
FIG. 19B is a perspective view of a single syringe body preform.
FIG. 20 is a perspective partial view of an alternative syringe body preform array.

One method of manufacturing syringe 300 is to fold over a single layer at the distal end 306 prior to molding, leaving upper and lower legs 302, 304 unjoined. This is illustrated in FIG. 19A, where syringe array 320 is shown to comprise preform bodies 322, 324, separated by groove 342 forming thin webs 343, 345. Concave blister halves 326, 340 are joined when surface 360 is bent over to seal with surface 358, bending at groove 334. Leg 332 is spaced from the bulk of the preform by angular leg portions 330, 336 so that a doubled guard is formed when the array is folded and then sealed.

A single syringe preform 324 is illustrated in FIG. 19B, with needle preform inserted in channel half 328, which combines with channel half 338 to seal needle preform base 347. After folding and sealing, the finished syringe would be filled by distal port 350 of needle sheath 344, which carries break-zone 346. Alternatively, the finished syringe may be filled by port 352, as shown in syringe preform 354 of FIG. 20.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures.

I claim:

1. A syringe for use with a target surface to be injected, comprising:

a needle comprising a sharpened distal end, a proximal end, and a fluid channel therebetween;

a primary cavity in fluid communication with said fluid channel, said primary cavity comprising at least one deformable wall;

a first flexible guard comprising a first base and a first tip, said first base substantially fixed relative to said needle, and said first tip extending past said sharpened distal end; and a second flexible guard comprising a second base and a second tip, said second base substantially fixed relative to said needle, and said second tip extending past said sharpened distal end;

wherein said sharpened distal end resides substantially between and behind said first tip and said second tip when the syringe is not in use; and wherein said first tip and said second tip make contact the with target surface to be injected prior to said sharpened distal end when the syringe is in use.

2. A syringe as recited in claim 1, wherein said needle comprises a proximal sheath base surrounding at least a portion of said proximal end of said needle.

3. A syringe as recited in claim 2, further comprising a needle sheath, said needle sheath comprising:
   a closed or sealed distal sheath end and an open proximal sheath end, said needle sheath enclosing said sharpened distal end of said needle, said open proximal sheath end sealed to said proximal sheath base; and
   a break-zone.

4. A syringe as recited in claim 2, further comprising:
   a needle sheath, said needle sheath comprising a closed or sealed distal sheath end and an open proximal sheath end, said needle sheath enclosing said sharpened distal end of said needle, said open proximal sheath end transitioning into said proximal sheath base, and comprising a weakened portion therebetween, whereby said weakened portion may be broken by twisting said needle sheath relative to said proximal sheath base.

5. A syringe as recited in claim 2, further comprising:
   a needle sheath, said needle sheath comprising a closed or sealed distal sheath end, an open proximal sheath end and a break-zone, said needle sheath enclosing said sharpened distal end of said needle, and said open proximal end sealing to said proximal sheath base.

6. A syringe as recited in claim 1, wherein said primary cavity is substantially filled with a liquid.

7. A syringe as recited in claim 6, wherein said liquid is under a positive pressure relative to atmospheric pressure.

8. A syringe as recited in claim 7, wherein said primary cavity comprises a surface indicator portion having positive curvature under said positive pressure, and negative curvature when said positive pressure is released, whereby the integrity of said liquid is indicated prior to use.

9. A syringe as recited in claim 8, wherein said surface indicator portion is a section of a sphere or ellipsoid.

10. A syringe as recited in claim 1, wherein said primary cavity comprises a first polymeric layer and a second polymeric layer, said first polymeric layer sealed to said second polymeric layer to form said primary cavity therebetween.

11. A syringe as recited in claim 10, wherein said first flexible guard and said second flexible guard are formed from at least one of said first polymeric layer and said second polymeric layer.

12. A syringe as recited in claim 1, further comprising:
   a sealed secondary cavity not in fluid communication with said primary cavity, said secondary cavity comprising at least one deformable wall; and
   a channel in fluid communication with said secondary cavity, said channel comprising a break-zone.

13. A syringe as recited in claim 12, wherein said break-zone can be broken by twisting.

14. A syringe, comprising:
   a needle comprising a sharpened distal end, a proximal end, and a fluid channel therebetween;
   a primary cavity in fluid communication with said fluid channel, said primary cavity comprising a first flexible polymeric layer and a second polymeric layer forming said primary cavity therebetween;
   a needle sheath, said needle sheath comprising a closed or sealed distal sheath end and an open proximal sheath end, said needle sheath enclosing said needle, said open proximal end sealed to said proximal end of said needle with a first fluid tight seal;
   a first break-zone located in said needle sheath, whereby twisting of said distal sheath end of said needle sheath separates said sheath from the syringe to expose said sharpened end of said needle;
   a first flexible guard comprising a first base and a first tip, said first base substantially fixed relative to said needle, and said first tip extending past said sharpened distal end; and
   a second flexible guard comprising a second base and a second tip, said second base substantially fixed relative to said needle, and said second tip extending past said sharpened distal end;
   wherein said sharpened distal end resides substantially in a first plane with said first flexible guard and said second flexible guard when the syringe is not in use.

15. A syringe as recited in claim 14, wherein said primary cavity is substantially filled with a first liquid.

16. A syringe as recited in claim 15, wherein said first liquid is under a positive pressure relative to standard atmospheric pressure.

17. A syringe as recited in claim 16, wherein said primary cavity comprises a surface portion having positive curvature under said positive pressure, and negative curvature when said positive pressure is released.

18. A syringe as recited in claim 14, further comprising:
   a secondary cavity not in fluid communication with said primary cavity, said secondary cavity comprising at least one deformable wall; and
   a secondary channel in fluid communication with said secondary cavity, said secondary channel comprising a second break-zone.

19. A syringe as recited in claim 18, wherein said second break-zone can be broken by twisting.

20. A syringe, comprising:
   a body comprising an upper layer and a lower layer;
   a needle comprising an axis, a sharpened distal end, a proximal end, and a fluid channel along said axis, said proximal end sealed to said body;
   a primary cavity between said upper and lower layers, wherein said primary cavity is in fluid communication with said fluid channel of said needle; and
   a first flexible guard comprising a first base and a first tip, said first base substantially fixed relative to said needle, and said first tip extending past said sharpened distal end;
   a second flexible guard comprising a second base and a second tip, said second base substantially fixed relative to said needle, and said second tip extending past said sharpened distal end; and
   wherein said sharpened distal end resides substantially between and behind said first tip and said second tip when the syringe is not in use.

21. A syringe as recited in claim 20, further comprising:
   a secondary cavity not in fluid communication with said primary cavity, said secondary cavity comprising at least one deformable wall;
   a secondary channel in fluid communication with said secondary cavity, said secondary channel comprising a break-zone;
   a fluid tight seal opposite said break-zone from said secondary cavity.

22. A syringe as recited in claim 20, further comprising:
   a needle sheath, said needle sheath comprising a closed or sealed distal sheath end and an open proximal sheath end, said needle sheath enclosing said needle, said open proximal end sealed to said proximal end of said needle with a first fluid tight seal; and
   a first break-zone located in said needle sheath, whereby twisting of said distal sheath end of said needle sheath separates said sheath from the syringe to expose said sharpened end of said needle.

23. A syringe, comprising:

a syringe body;

a hollow needle comprising a sharpened tip and a base, said base fixed to said syringe body;

a fluid chamber within said syringe base, wherein said fluid chamber is in fluid communication with said needle; and a bifurcated guard extending from said syringe body, said bifurcated guard comprising first and second tips that extend past said sharpened end of said needle, said first and second tips lying on either side of said needle in a first plane.

24. A syringe as recited in claim 23, further comprising sheath means for protecting said needle.

25. A syringe as recited in claim 24, wherein said syringe body is comprised of a first polymeric layer and a second polymeric layer sealed together to form said fluid chamber.

26. A syringe as recited in claim 25, wherein said fluid chamber is penetrated by said base.

27. A syringe as recited in claim 25, wherein said first polymeric layer and said second polymeric layer are sealed around at least said sharpened tip of said needle to form a needle sheath, said needle sheath having a weakened portion to serve as a break-zone.

28. A syringe as recited in claim 25, wherein the syringe is attached to at least a second like syringe by a thinned web formed of at least one of said first polymeric layer and said second polymeric layer.

* * * * *